United States Patent
Elstrom

[19]

[11] Patent Number: 5,999,847
[45] Date of Patent: Dec. 7, 1999

[54] APPARATUS AND METHOD FOR DELIVERY OF SURGICAL AND THERAPEUTIC AGENTS

[76] Inventor: John A. Elstrom, 466 Illinois Rd., Lake Forest, Ill. 60045

[21] Appl. No.: 08/955,350

[22] Filed: Oct. 21, 1997

[51] Int. Cl.⁶ .................................................... A61N 1/30
[52] U.S. Cl. ............................................. 604/20; 604/21
[58] Field of Search ........................... 604/19–22; 606/7, 606/15, 16, 9; 607/88, 89

[56] References Cited

U.S. PATENT DOCUMENTS

| | | |
|---|---|---|
| 4,819,751 | 4/1989 | Shimada et al. . |
| 4,945,050 | 7/1990 | Sanford et al. . |
| 5,036,006 | 7/1991 | Sanford et al. . |
| 5,100,792 | 3/1992 | Sanford et al. . |
| 5,141,131 | 8/1992 | Miller, Jr. et al. . |
| 5,267,985 | 12/1993 | Shimada et al. . |
| 5,286,254 | 2/1994 | Shapland et al. . |
| 5,304,120 | 4/1994 | Crandell et al. . |
| 5,371,015 | 12/1994 | Sanford et al. . |
| 5,421,816 | 6/1995 | Lipkovker . |
| 5,439,440 | 8/1995 | Hofman et al. . |
| 5,445,611 | 8/1995 | Eppstein . |
| 5,478,744 | 12/1995 | Sanford et al. . |
| 5,498,238 | 3/1996 | Shapland et al. . |
| 5,507,724 | 4/1996 | Hofman et al. . |
| 5,658,892 | 8/1997 | Flotte et al. ............................. 514/44 |
| 5,836,940 | 11/1998 | Gregory .................... 604/20 |

OTHER PUBLICATIONS

Waksman, Ron "Local Catheter–Based Intracoronary Radiation Therapy for Restenosis", Am J Cardiol., 78 (Suppl 3A): 23–28, 1996.

*Primary Examiner*—Wynn Wood Coggins
*Assistant Examiner*—Sharon Finkel
*Attorney, Agent, or Firm*—McDonnell Boehnen Hulbert & Berghoff

[57] ABSTRACT

Localized, transient pressure waves are applied to tissue adjacent to target cells by means of a light source and a coupling interface placed in contact with the tissue that converts light from the light source into acoustic energy. The pressure waves cause transient poration of the cell membranes. The therapeutic agents are delivered to the site of the localized pressure waves by any suitable means, such as by injection with a needle. The light source and coupling interface can be incorporated into a catheter for application of the pressure waves to diseased blood vessels. A manually manipulable surgical device incorporating a needle for injecting the agent, light source, and coupling interface is also described.

4 Claims, 2 Drawing Sheets

APPARATUS AND METHOD FOR DELIVERY OF SURGICAL AND THERAPEUTIC AGENTS

BACKGROUND OF THE INVENTION

A. Field of the Invention

The present invention relates to the treatment of disease or ailments in humans or animals. More particularly, the invention relates to a method and apparatus to deliver surgical or therapeutic compounds such as drugs and genes into cells of human or animal tissues.

B. Description of Related Art

Gene therapy represents a promising modality for the treatment of a variety of acquired and inherited diseases afflicting humans of all ages. The therapy involves the introduction of genes into cells so as to correct for defective genes responsible for the cause of the ailment or disease. There are two approaches to performing gene therapy; ex-vivo and in-vivo. Ex-vivo requires the harvesting of cells, introduction of genes into harvested cells, and subsequent implantation of cells back into the human or animal body. In-vivo gene therapy negates the need to harvest cells since direct injection of genes into tissues is more convenient as a treatment modality. In-vivo gene therapy is desirable since it resembles conventional drug therapy.

There are several methods of gene delivery required in conjunction with in-vivo gene therapy. These methods serve to introduce the desired genes into patient cells. The most promising for high efficiency of gene expression is the use of a viral vector. A viral vector contains the therapeutic gene attached to a key promoter of an attenuated virus. Once introduced into tissue, a viral particle infects a cell lacking the desired gene and subsequently incorporates the therapeutic gene within the genetic system of the cell. But the use of a viral vector introduces issues of toxicity and safety since viral vectors can produce protein products that are allergenic to the patient as well as the possibility of causing uncontrolled growth by random translocation. Therefore the use of non-viral gene delivery methods are more desirable for the future.

Recently it was discovered that direct injection of plasmid DNA into skeletal muscle can be taken up by muscle cells and be expressed in animal cells. Direct injection of genetic material into tissues should alleviate the issues of toxicity and safety in humans but the efficiency of expression of the plasmid DNA is rather low. This is attributable to the low amount of plasmid DNA that actually get transported through cell membranes and subsequently make their way to the nuclei of cells. Thus, there exists the need to enhance transport of genetic materials into intracellular space as well as transport to the vicinity of the nucleus.

Several chemical and physical methods have been applied with direct injection of genes to enhance the efficiency of gene uptake and subsequent expression. The chemical methods range from combining the naked DNA with calcium phosphate precipitate to the use of liposomes and receptor-mediated molecules. The physical methods range from electroporation to biolistic transport.

Electroporation uses brief electrical pulses produced by electrodes in the range of kV/cm to create transient pores in cell membranes located between the electrodes. Biolistic transport is the bombardment of cells or tissues with particles coated with DNA. The particles are accelerated into tissue by devices analogous to guns. The guns generate explosive acceleration by either using very high pressure gases or by electric field discharge. These physical gene delivery methods have demonstrated practical utility for in-vitro transfection of animal and plant cells and limited in-vivo transfection of animal and human tissues.

Although electroporation and biolistics have demonstrated practical gene delivery into tissues, their use on human tissues are limiting by the nature of their means of implementation. Electroporation uses very high voltage potentials and requires that the cells be placed in between the electrodes. Gene delivery into confined spaces such as the inner walls of blood vessels and arteries is problematic due to limited working spaces and relatively delicate nature of the tissues. High voltages placed on the surface of tissues such as skin will produce damage due to excessive heating and dielectric breakdown. Particle acceleration into tissues is limiting by the use of guns requiring high gas pressure and electric discharge to accelerate them. These requirements tend to produce devices, although hand-held, that are relatively large and limit their application to superficial distances from the tissues as well as in confined spaces such as blood vessels or in various cavities of the body such as the lungs. Thus there exists a need for method and device that can effect membrane permeability with relatively less traumatic means as well as providing easy access to confined, or spaces deep within animal and human organs. Ultimately the method and apparatus serve to enhance the uptake and subsequent expression of direct injection gene therapy.

Patents of interest related to the present invention include the patents issued to Sandford et al., U.S. Pat. Nos. 5,487,744, 5,371,015, 5,100,792 and 5,036,006; the patents to Shimada et al., U.S. Pat. No. 4,819,751; Shimada et al., U.S. Pat. No. 5,267,985; Lipkover, U.S. Pat. No. 5,421,816; Shapland et al., U.S. Pat. No. 5,286254; Shaplan et al., U.S. Pat. No. 5,498,238; Eppstein et al., U.S. Pat. No. 5,445,611; the patents to Hoffinann et al., U.S. Pat. Nos. 5,439,330 and 5,507,724; Crandell et al., U.S. Pat. No. 5,304,120 and Miller, Jr., U.S. Pat. No. 5,141,131.

SUMMARY OF THE INVENTION

A device and methods are provided for using stress and thermal confinement of light energy to enhance membrane permeability and subsequent transport of surgical and therapeutic agents such as naked DNA or drugs into the intracellular spaces of plant structures, animal, and human tissues.

In one aspect of the invention, a device is provided for delivering therapeutic agents into cells of body. The device is for use in conjunction with a source of therapeutic agents delivered to tissue in the vicinity of the cells. The device comprises a light source, such as laser, emitting radiation and a coupling interface receiving the radiation from the light source. The radiation and coupling interface are positioned adjacent to the body such that the coupling interface is in contact with the tissue. The light source and coupling interface cooperate to responsively generate a localized, transient pressure wave in the tissue of the body so as to cause transient poration of the membrane of said cells, whereby the transient poration of the membrane permits the therapeutic agents to be assimilated into the cells.

An object of this invention is to provide an apparatus and method of producing mechanical wave gradients, in-vivo, to create transient poration of cell membranes, and to transport surgical and therapeutic agents into the vicinity of the cell nucleus.

One embodiment of this invention provides an apparatus for the introduction of surgical and therapeutic agents into the cells of the organ of skin.

Another embodiment of this invention provides a surgical needle capable of delivering the surgical agents, therapeutic agents, absorbing dyes, and particulates, and the stress waves into the vicinity of direct injection.

Yet another embodiment of the invention provides for the creation of shock waves within a liquid reservoir or tissues to accelerate particulates having the surgical or therapeutic agents attached to the particulates into intracellular space of animal and human tissues.

Yet another embodiment of the invention is a catheter having reservoirs for the surgical, therapeutic agents, dyes, and particulates in combination with means for producing shock waves to accelerate particulates into peripheral tissues of blood vessels and tissues of human organs.

BRIEF DESCRIPTION OF THE DRAWINGS

Presently preferred embodiments of the invention are described below in conjunction with the appended drawing figures, in which like reference numerals refer to like elements in the various view, and in which.

DETAILED DESCRIPTION OF THE PREFERRED EMBODIMENTS

Figure 1:
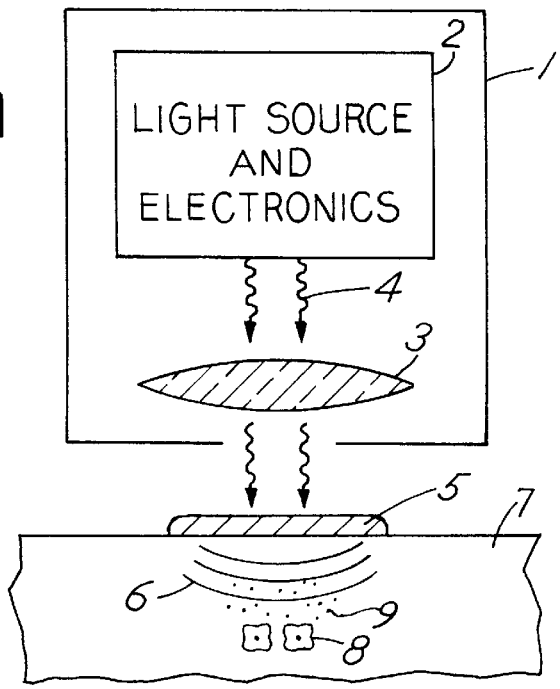
FIG. 1 is a schematic representation of a apparatus generating a stress wave to effect cell membrane permeability.

Referring to FIG. 1, a first embodiment of the apparatus includes a drug delivery device 1 containing a laser light source and electronics 2 to control the operation of the light source. Element 2 is capable of providing a light beam 4 of a specific duration and amount of specific energy level. The characteristics of the light beam are determined by a beam conditioner 3. The beam conditioner 3 contains elements that determine the beam diameter, the distance of the focal spot, and the intensity distribution of the beam across its diameter.

The light beam 4 is directed through a coupling interface 5. The coupling interface 5 facilitates the transfer of light energy into mechanical pressure waves. The coupling interface can be a rigid material having optical absorption properties sufficient to produce stress waves (i.e., mechanical pressure or acoustic waves) when a brief pulse of light is applied within the material. The coupling interface 5 can be a reservoir containing various solutions having different optical absorption properties. The light beam 4 is applied within human tissue 7 to produce a propagating mechanical pressure wave gradient 6. The mechanical wave gradient provides a means of creating transient poration of cell membranes within the tissue.

The drug delivery device 1 is used in combination with direct injection and parenteral administration of surgical and therapeutic agents for isolation and local delivery of the agents 9 into cells 8. The process proceeds as follows: after introduction of the surgical and therapeutic agents into a local tissue region, the light beam 4 of the device 1 is applied in the vicinity of the location of administration. The light beam 4 and coupling interface 5 produces mechanical wave pressure gradients that effect cell permeability by transferring radial, circumferential, longitudinal and shear stress so as to deform the cells 8. Cell volume deformation produces transient stresses on cell membranes due to a differential change in surface area.

The pressure gradients affecting cell membranes are produced in a controlled manner by manipulating the characteristic of the light energy deposition process into the coupling interface 5 and/or tissue. The conversion of light energy into mechanical waves is governed by the process of thermal elastic expansion in the coupling interface material 5. When light energy is applied in a brief manner to a material or medium, heat is generated which is converted into acoustic waves as the energy is dissipated to the surrounding medium. Stress generation is governed by the thermal diffusion and the speed of sound of a material or medium. Depending on the time duration of a pulse of light, high stress or pressure can be generated in a medium. For effective delivery, light of sufficient energy is applied so as to not create pressure waves sufficient to permanently damage or lyse the cells.

Stress generation by confinement is the preferred method of production due to its relatively small increase in temperature. The laser pulse heats the coupling interface medium much faster than the time required for the stress waves to propagate through the irradiated volume. A dimensionless parameter of stress confinement is the product of the optical absorption coefficient, the speed of sound, and the laser pulse duration. This parameter can be used to determine the degree of confinement. The energy per area of a light pulse and its repetition rate can be used to create a stress gradient within a specific region of tissue as the mechanical waves travel from the irradiated spot. The boundary of the irradiated medium also determines reflected waves that can provide tensile stresses to tissues within a location.

In addition to the creation of the transient poration of cell membranes, the propagating acoustic waves, which have very high frequencies, create microstreaming motions within regions containing liquid such as extracellular space of tissue and intracellular space of cells. Since microstreaming is proportional to acoustic absorption, the high frequencies can promote effective microstreaming forces due to rapid attenuation of the propagating wave. The microstreaming forces can result in circular motion of the extracellular liquid and the cell cytoplasm. This motive action can enhance transport of the delivered agents into the intracellular space as well as toward the nucleus of the cell. Microstreaming increases the probability of the agents to be transported into nucleus of the cell.

One mode of practice of confined stress generation of acoustic waves is the use of a Nd:YAG laser operating in a Q-switched mode (Model YG 681, Quantel International, Santa Clara, Calif.). The device is used to create stress waves in skin tissue to deliver genes or therapeutic agents into skin cells to cure a variety of skin diseases such as cancer and psoriasis after direct injection or topical application of the agents. Short laser pulses, with duration of nanoseconds to microseconds, can be applied to a localized area within tissue. In some applications, the coupling interface can be used to generate the stress gradient within the coupling interface. The stress gradient then propagates into the underlying tissues. The coupling medium serves to enhance coupling of the acoustic waves into the underlying tissues. The coupling medium 5 can be a solid-like glass doped with absorption centers or a liquid such as a buffer. The buffer can also contain non-irritating dyes that serve as the absorption medium and the surgical or therapeutic agents needing delivery.

Figure 2:
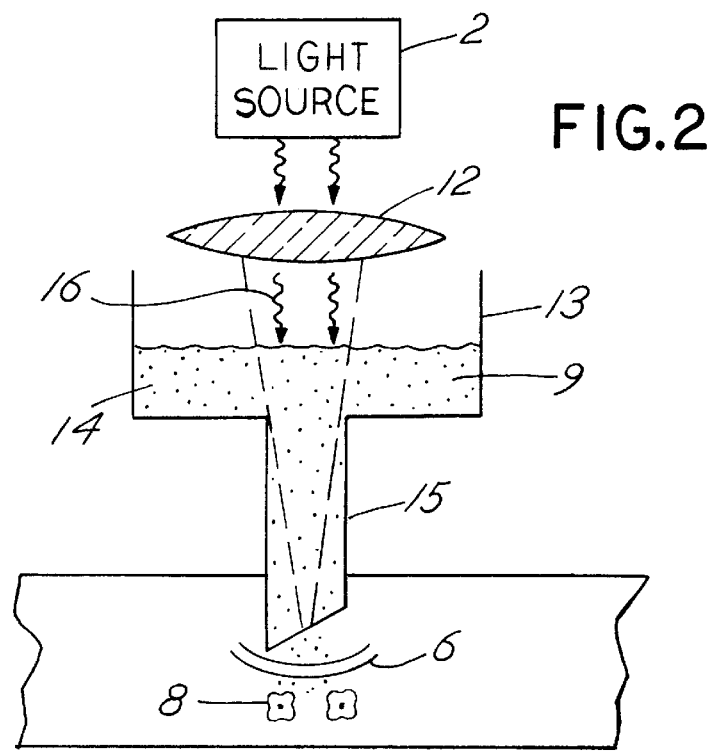
FIG. 2 is a schematic representation of a needle apparatus providing injection into tissue or joint spaces in combination with delivering light energy into the vicinity of injection.
Figure 3A:
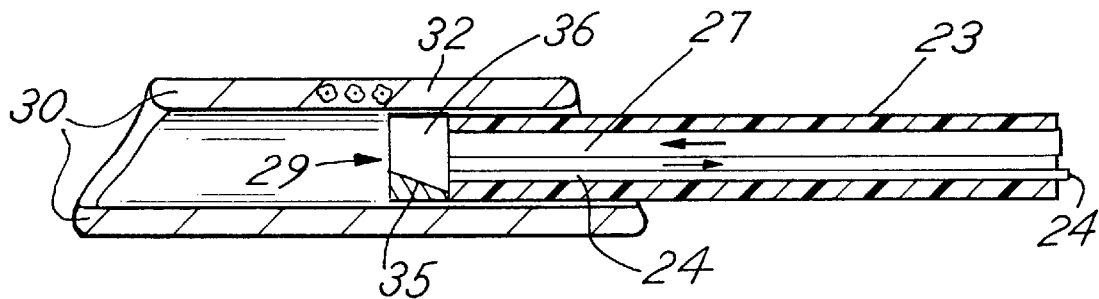
FIGS. 3A and 3B are schematic representations of catheter apparatus for providing agent delivery into the periphery of diseased vessels.
Figure 3B:
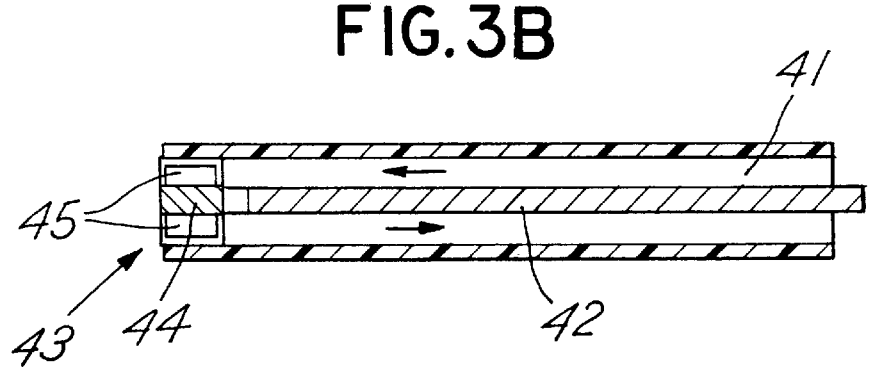

Referring to FIG. 2, a second embodiment of the invention includes a light source 2 that produces a pulse of light beams 16 modified by a focusing element 12 through a reservoir barrel 13 resembling a syringe and a needle 15 to produce pressure waves in the vicinity of injection inside tissue 7. The light beam 16 traverses a solution 14 containing the surgical or therapeutic agent 9 and/or absorption enhancement dye or particulates coated with the therapeutic agents.

The method of application of the second embodiment, described above, preferably is accompanied by the simultaneous injection of the therapeutic agents into tissue and delivery of short pulses of light into the tissue space. As the agents 9 are injected into tissue the generation of pressure waves 6 create stresses as to permeate the cell membranes of the surrounding tissue. A non-irritating, non-toxic dye having the appropriate absorption can also be mixed with the agents as to enhance the conversion of light energy into mechanical waves.

Another method of application is to inject coated and non-coated particulates heterogeneous in size having a defined absorption coefficient such as carbon particles into the tissue using the needle device. A shock wave is generated using the light source with sufficient energy density and temporal duration to accelerate agent-coated particulates into the surrounding cells. The non-coated particles having larger sizes are used to facilitate the creation of shock waves due to rapid thermal expansion created by absorption of light energy from the laser beam. The particle-liquid-air interface will provide a means of generating tensile stress within the particles as to generate shock waves. The shock wave produces an explosion that accelerates small agent coated particles into the cells as it propagates outward to the surrounding tissues.

To facilitate the optical set-up for light delivery, the needle device 13/15 can be modified by placing the plunger or piston used to push fluid such that its axis is either perpendicular to the axis of the light beam or at some other appropriate angle. The light beam 16 can also be delivered with a fiber optic filament that is axially aligned with the needle axis. The fiber can have focusing elements at its tip or it can have a flat profile of light intensity. This embodiment would enable easy transfer of direct injection of agents in combination with mechanical wave generation at joint spaces such as knee joints or deep within the body.

Referring to FIG. 3A, another embodiment is illustrated wherein the gene or therapeutic agent is delivered with a catheter 23 containing a fluid conduit 27 and an optical fiber 24 to a site within a blood vessel 30. The tip of the catheter 23 contains a cap 29 having a reflective surface 35 and a cavity 36. The reflective surface 35 directs the light pulse exiting the fiber into the direction perpendicular to the axis of the catheter. The cavity 36 provides fluid access to the adjacent diseased vessel tissues 32. The fluid conduit 27 contains an entering path and an exit path forming a loop within the cavity 36. The fluid conduit provides fluid circulation and the delivery of a bolus containing the therapeutic agents is synchronized with the application of the light pulse during agent delivery into the cells of the vessel tissues 32.

FIG. 3B is a variation of the catheter for delivery of genes of therapeutic agents within a diseased blood vessel. The catheter contains an optical fiber 42 that conducts light energy to an optically absorbent element or coupling interface 44. The optical absorbing element 44 is contained in a tip 43 which also has a cylindrical cavity 45. Cavity 45 is connected to a conduit 41 that provides fluid entrance and exit. The conduit can transport fluid containing agent-coated particulates such as gold or tungsten.

A shock wave is generated using the light energy delivered to the absorbing element 44. Ablation of a small amount of the absorbing element 44 may occur, which facilitates the creation of a tensile stress which adds to the compression stress. The spallation of the ejected mass creates a shock wave that propagates in a radial direction. The shock wave accelerates the particulates that are synchronously delivered to the cavity 43. The accelerated particles travel radially into the surrounding tissues of the blood vessel. The particles penetrate through the cell membranes without lysis. Another means is to coat the inner wall of the cylindrical cavity 45 coated particulates. The shock wave is produced within element 44 that subsequently transfers its energy to accelerate the particles off the wall and into the cells of the tissues of the periphery of the blood vessel.

To provide ease of use of the above described embodiments, an agent delivery device comprising light source, coupling interface and therapeutic agent source may be manufactured as a unitary implement incorporating a compact handle. The device can also be incorporated into a "gun" by the use of compact laser diodes. The principle and device can be combined with minimally invasive imaging or scopes to administer gene therapy to various cavities within the human body. Although the preferred embodiment discloses a specific laser for illustrative purposes, it is understood by the person of ordinary skill in the art that wavelengths ranging from 190 nm to 3000 nm can be used to generate pressure waves. The time duration of picoseconds to seconds can be used. The temperature created in tissue can range from 20 degrees Celsius to 100 degrees Celsius. Since stress produced is proportional to temperature, it is understood that in order to prevent cell lysis, temperature within the physiologically tolerable range should be used.

I claim:

1. A device for delivering genetic material into the interior of cells of body for the purpose of expression of a protein by said cells, said device for use in conjunction with a source of said genetic material delivered to tissue of said body in the vicinity of said cells, comprising:

a light source emitting radiation;

a coupling interface receiving said radiation from said light source, said radiation and coupling interface cooperating to responsively generate a localized, transient pressure wave in tissue in said body at an intensity level so as to cause a transient poration of the membrane of said cells without permanently lysing or damaging said cells; said light source and coupling interface operative to produce said localized, transient pressure wave when they are positioned adjacent to said body such that said coupling interface is in contact with said body, wherein said transient poration of said membrane of said cells permits said genetic material to be assimilated into said cells; and wherein said genetic material is coated to particulates, and wherein said pressure wave accelerates said particulates into said cells thereby delivering said genetic material into said cells.

2. The device of claim 1, wherein said particulates are selected from the group consisting of gold and tungsten particulates.

3. A device for delivering genetic material into the interior of skin cells of a body in a manner so as to not cause any permanent damage to said skin cells and allow said skin cells to express a protein associated with said genetic material, said genetic material delivered to tissue of said body in the vicinity of said skin cells, comprising:

a light source emitting radiation;

a coupling medium placed on the surface of the skin, said coupling medium receiving said radiation from said light source, said radiation and coupling interface cooperating to responsively generate a localized, transient pressure wave in said tissue in said body at an intensity level so as to cause a transient poration of the membrane of said cells without permanently damaging said cells;

wherein said transient poration of said membrane of said cells permits said genetic material to be introduced within and assimilated into said cell; and wherein said genetic material is bonded to particulates and wherein said genetic material is introduced within and assimilated into said cell in a condition bonded to said particulates.

4. A device for delivering genetic material into the interior of skin cells of a body in a manner so as to not cause any permanent damage to said skin cells and allow said skin cells to express a protein associated with said genetic material, said genetic material delivered to tissue of said body in the vicinity of said skin cells, comprising:

a light source emitting radiation;

a coupling medium placed on the surface of the skin, said coupling medium receiving said radiation from said light source, said radiation and coupling interface cooperating to responsively generate a localized, transient pressure wave in said tissue in said body at an intensity level so as to cause a transient poration of the membrane of said cells without permanently damaging said cells;

wherein said transient poration of said membrane of said cells permits said genetic material to be introduced within and assimilated into said cell; and wherein said genetic material is bonded to particulates selected from the group of gold and tungsten particulates and wherein said genetic material is introduced within and assimilated into said cell in a condition bonded to said particulates.

\* \* \* \* \*